United States Patent [19]

Epshetsky

[11] Patent Number: 5,327,775

[45] Date of Patent: Jul. 12, 1994

[54] CONDOM TESTER AND APPLICATOR

[75] Inventor: Yefim Epshetsky, San Francisco, Calif.

[73] Assignee: Yakov Epshteyn, San Francisco, Calif. ; a part interest

[21] Appl. No.: 967,290

[22] Filed: Oct. 27, 1992

[51] Int. Cl.⁵ ............................................. G01M 3/02
[52] U.S. Cl. ...................................................... 73/40
[58] Field of Search ........................................... 73/40

[56] References Cited

U.S. PATENT DOCUMENTS

| | | | |
|---|---|---|---|
| 2,567,926 | 9/1951 | Dunkelberger | 73/40 X |
| 4,872,463 | 10/1989 | Nishizono | 128/844 |
| 4,875,358 | 10/1989 | Marsh et al. | 73/40 |
| 4,987,905 | 1/1991 | Broad | 128/844 |
| 5,097,697 | 3/1992 | Carnal et al. | 73/40 |
| 5,129,256 | 7/1992 | McGlothlin | 73/40 |

Primary Examiner—Hezron E. Williams
Assistant Examiner—Joseph W. Roskos
Attorney, Agent, or Firm—David Pressman

[57] ABSTRACT

A condom tester and applicator comprises a hollow cylinder (10) having an open proximal end (12) and a distal end (14). The hollow cylinder is constructed of a transparent material, such as clear plastic. The distal end of the cylinder possesses an end-face (16) which contains a one-way valve (18). The inner surface of the hollow cylinder accommodates a plurality of longitudinal grooves (22). A mounting flange (24) is formed at the periphery of the proximal end of the hollow cylinder. A condom is tested by sealingly installing it into the hollow cylinder and creating a pressure differential across the condom membrane by forcing out the air inside the cylinder through the one-way valve and thus distending the condom. The condom is donned onto a penis by inserting the penis inside the hollow cylinder with the condom inflatably installed therein, and transferring the hem ring of the condom from the mounting flange onto the base of the penis.

21 Claims, 5 Drawing Sheets

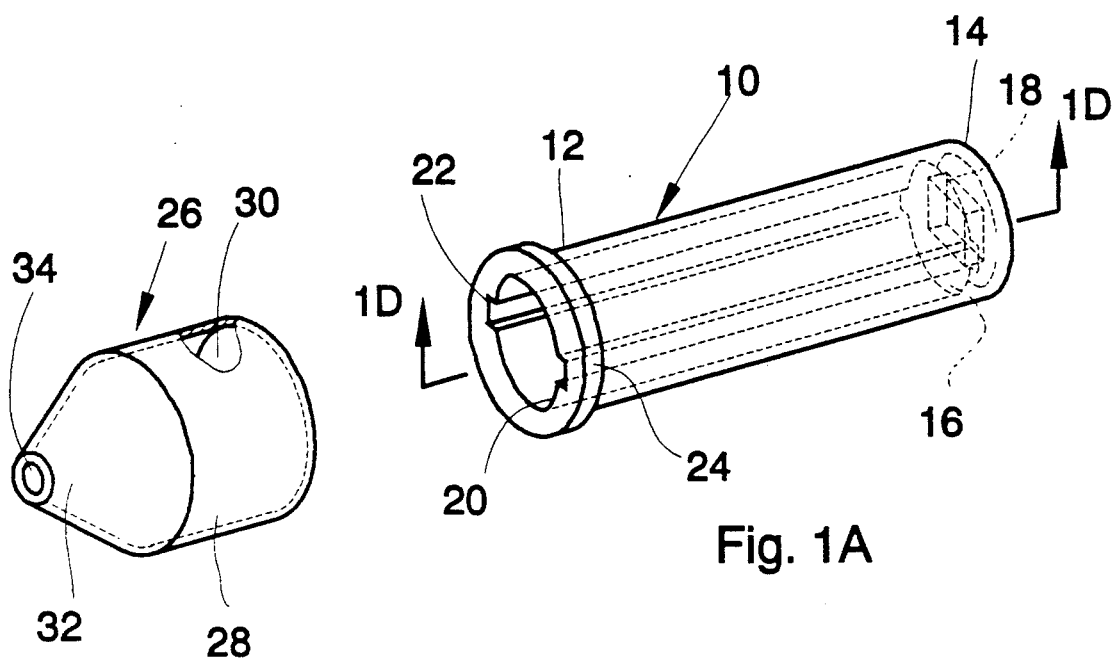
Fig. 1A
Fig. 1B
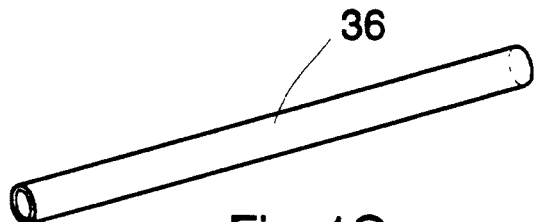
Fig. 1C
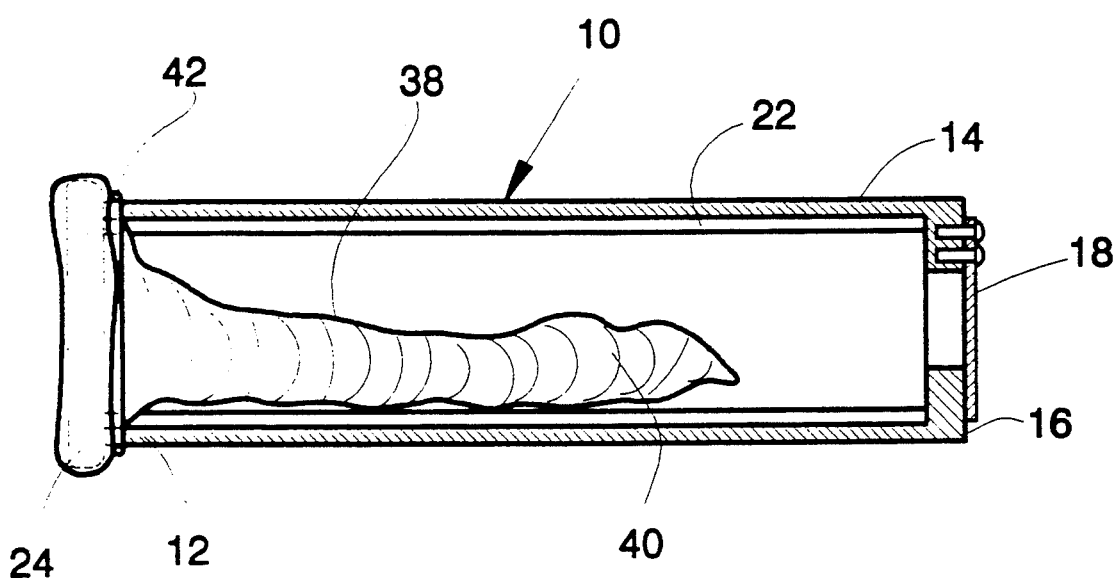
Fig. 1D

CONDOM TESTER AND APPLICATOR

BACKGROUND—

1. Field of the Invention

The present invention relates to the field of condom testing and application, particularly to mechanical condom testers and applicators.

2. Description of Prior Art

Condoms have long been used for contraceptive purposes and are of ever increasing importance in reducing the dissemination of sexually transmitted diseases. Moreover, with the advent of such deadly viruses as Acquired Immune Deficiency Syndrome (AIDS), it has become crucial to encourage the use of condoms. This can be accomplished by making condom application quick and convenient and by providing the users with added confidence in the quality and effectiveness of condoms.

Currently, a plurality of condom testers and applicators are known and used for these purposes.

U.S. Pat. No. 4,872,463 to Taiji Nishinozo, 1989, discloses a condom applicator which comprises a flexible continuous strip having a centrally located longitudinal slot and pull tabs attached to the strip near the slot. Both ends of the strip are rolled together with the condom into a disk. To apply the condom, the user pulls the tabs backwards along the penis to unroll the condom sheath over it.

A similar applicator device comprising a pair of strips which are pulled to unroll a condom is described in U.S. Pat. No. 4,987,905 to Robert Broad, 1991.

However, both applicators require that the penis be fully erect in order to unroll the condom. Moreover, the application of the condom is not instantaneous and demands a rolling motion which takes time and which may be unpleasant to the user because of the initial rolling contact with a cold sheath. Furthermore, these applicators are utilized only for donning condoms, and their function does not include testing the integrity of the condom sheath.

Several different methods and devices for testing condoms are currently available.

One such tester is set forth in U.S. Pat. No. 4,875,358 to Marsh et al., 1989. This device consists of a hollow cylinder having a distal end furnished with an opening and a proximal end fitted with a bellows which contains a one-way valve. For testing, a condom is placed over the distal end and is gradually unrolled along the outside walls of the hollow cylinder. The hem ring of the condom is then sealingly retained in a groove situated near the proximal end of the hollow cylinder. The user than actuates the bellows to pump air into the hollow cylinder and out the opening located in its distal end to inflate the condom, which is then inspected for leaks.

However, this tester has several notable drawbacks. Not only does it lack the capability to aid the user in applying the condom, but it complicates the process even further. Once the condom has been unrolled, it is difficult to roll it back into a taut disk. The subsequent application of the condom is cumbersome if it is not rolled back properly.

OBJECTS AND ADVANTAGES

It is accordingly an object of the invention to provide a condom tester and applicator which quickly and accurately tests the integrity of a condom sheath, which allows the user to apply a condom instantaneously, which suspends a tested condom in a state ready for immediate application, which has a compact and simple construction, which is convenient in use, and which is easy and inexpensive to manufacture. Further objects and advantages will become apparent after consideration of the ensuing description and the accompanying drawings.

DRAWING FIGURES

FIGS. 1A to 1C are perspective views of a condom tester, applicator, and air expeller according to the present invention.

FIG. 1D is a cross-sectional view of the condom tester and applicator of FIG. 1 in the direction indicated by lines 1D—1D of FIG. 1A, showing the tester and applicator with an untested condom.

Figure 1E:
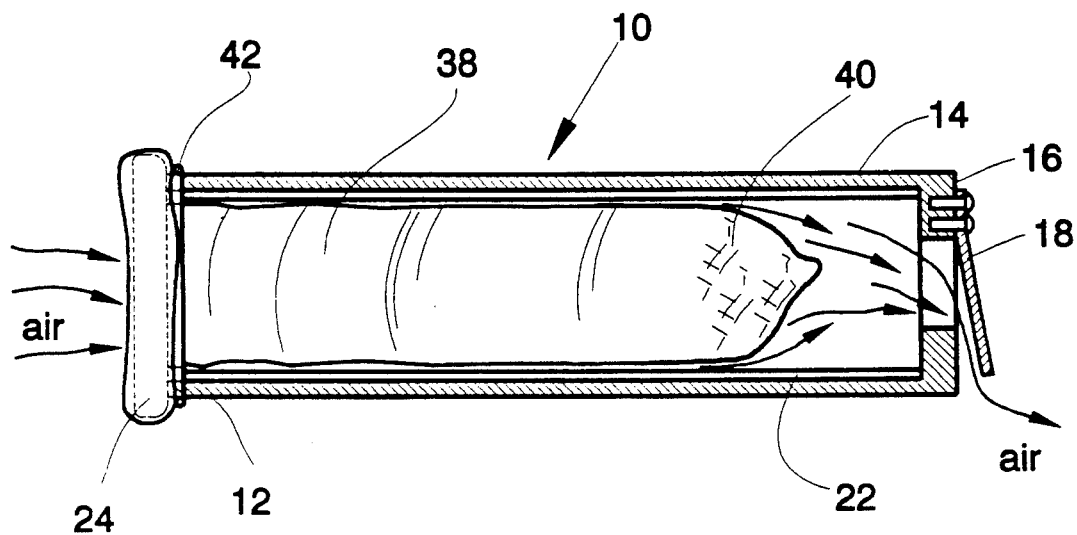
FIG. 1E shows the condom tester and applicator of FIG. 1D with an inflated condom.

REFERENCE NUMERALS USED IN DRAWINGS AND DESCRIPTION 10, 98—hollow cylinders
12—open proximal end
14—distal end
16, 70—end-faces
18, 72, 106, 130—check valves
20—inner surface
22, 62, 74, 86—longitudinal grooves
24, 54, 104, 128—mounting flanges
26—mouthpiece
28—hollow cylindrical portion
30—open end
32—conical portion
34—aperture
36—flexible tube
37—penis
38—condom sheath
40—condom head
42—hem ring
44—telescopically foldable cylinder
46—proximal conical element
48—distal conical element
49—medial conical elements
50, 68, 78—tapered ends
52, 66, 76—flared ends
56, 80, 114—through central openings
58, 82, 94—O-rings
60, 84, 96—annular grooves
64, 100, 122—blind central openings
88—manual bellows
90—cylindrical cap 92—flexible tube
102—perforated core
108—raised annular portion
110—conical chamfer
112—lubrication valve
116—conical flared portion
118—test openings
120—cylindrical member
124—air chamber
126—nipple
132—raised longitudinal strips FIG. 1—Condom Tester and Applicator—Description A perspective view of a condom tester and applicator according to the present invention is shown in FIGS. 1A and 1B.

The condom tester and applicator comprises a hollow cylinder 10 having an open proximal end 12 and a distal end 14. Cylinder 10 is constructed of a transparent material, e.g., clear plastic. Distal end 14 possesses an end-face 16 which contains a flap-type check valve 18. Valve 18 serves as a one-way valve, letting air out from the interior of cylinder 10. An inner surface 20 of cylinder 10 has a plurality of longitudinal grooves 22. A mounting flange 24 is formed at the periphery of proximal end 12.

A mouthpiece 26 may be used in conjunction with cylinder 10. Mouthpiece 26 contains a hollow cylindrical portion 28 with an open end 30 and a conical portion 32, which has an aperture 34 at its apex. The inside diameter of portion 28 is slightly larger than the outside diameter of flange 24, such that mouthpiece 26 fits over proximal end 12 of cylinder 10.

A flexible tube 36 (FIG. 1C) may also be utilized with cylinder 12 to expel air which may become trapped between a condom sheath and a male penis (not shown). Tube 36 may be made of rubber or flexible plastic.

In one specific embodiment of the invention, cylinder 10 is approximately 20 cm long and 6 cm in diameter. The inside diameter of cylinder 10 is about 5.5 cm and the depth of grooves 22 is approximately 1.5 mm. Tube 36 is about 25 cm long.

FIGS. 1 through 1B—Condom Tester and Applicator—Operation

To test and apply a condom, the user inserts an unrolled condom sheath 38 into cylinder 10 (FIG. 1D), such that a condom head 40 enters cylinder 10 first. A hem ring 42 of sheath 38 is then sealingly wrapped around flange 24.

Figure 1F:
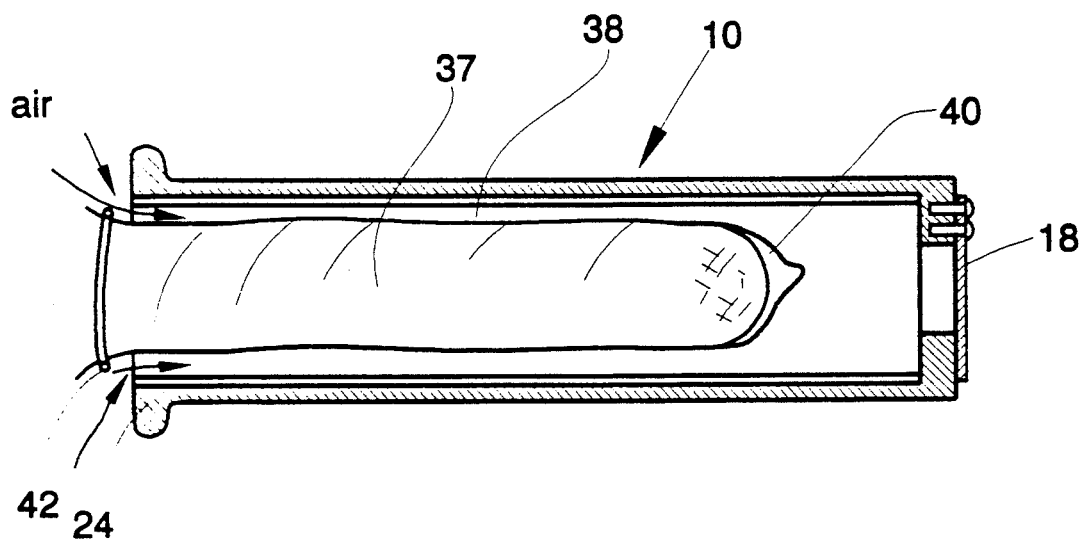
FIG. 1F shows the condom tester and applicator of FIG. 1E being used to apply a condom.

The user then inflates sheath 38 by blowing air into open end 12 of cylinder 10 (FIG. 1E). If the user wishes to avoid lip contact with sheath 38, mouthpiece 26 may be fitted onto the proximal end of cylinder 10. If mouthpiece 26 is utilized, hem ring 42 provides a seal between the inner surface of portion 28 and the periphery of flange 24.

As sheath 38 is inflated, it displaces air from the interior of cylinder 10 through valve 18. If head 40 of the condom sheath distends prematurely, grooves 22 channel the air, which may become trapped between hem ring 42 and head 40, out through valve 18. Once the condom is fully stretched, the user stops forcing air into the cylinder and valve 18 shuts automatically. Due to the pressure differential across the condom membrane, sheath 38 is thus suspended in a dilated state and may be inspected for leaks through the transparent walls of cylinder 10. Any change in the shape and size indicates that sheath 38 is defective.

To apply the condom onto a penis 37 (FIG. 1F), the user inserts the penis into sheath 38 within cylinder 10. The insertion of penis 37 into sheath 38 is effortless, since the walls of the sheath are maintained flush with inner surface 20 of cylinder 10 by a pressure differential across the membrane of sheath 38. The user than pulls hem ring 42 off of flange 24 towards the base of the penis, thereby eliminating the pressure differential across sheath 38. Sheath 38 is then instantly donned.

In order to ensure complete expulsion of air from the applied condom, the user may insert tube 36 (FIG. 1C) into the condom prior to inserting his penis in sheath 38 when it is inside cylinder 10. After application of the condom, any air trapped inside sheath 38 escapes through tube 36, which is then pulled out. Prior to insertion, tube 36 may be lubricated to facilitate its removal.

The above-described condom tester and applicator quickly tests the integrity of a condom sheath, permits the user to apply a condom instantaneously, and allows suspension of a tested condom in a state ready for immediate application. The device is convenient in use, simple in construction, and is inexpensive to manufacture.

FIG. 2—Collapsible Condom Tester and Applicator—Description

Figure 2A:
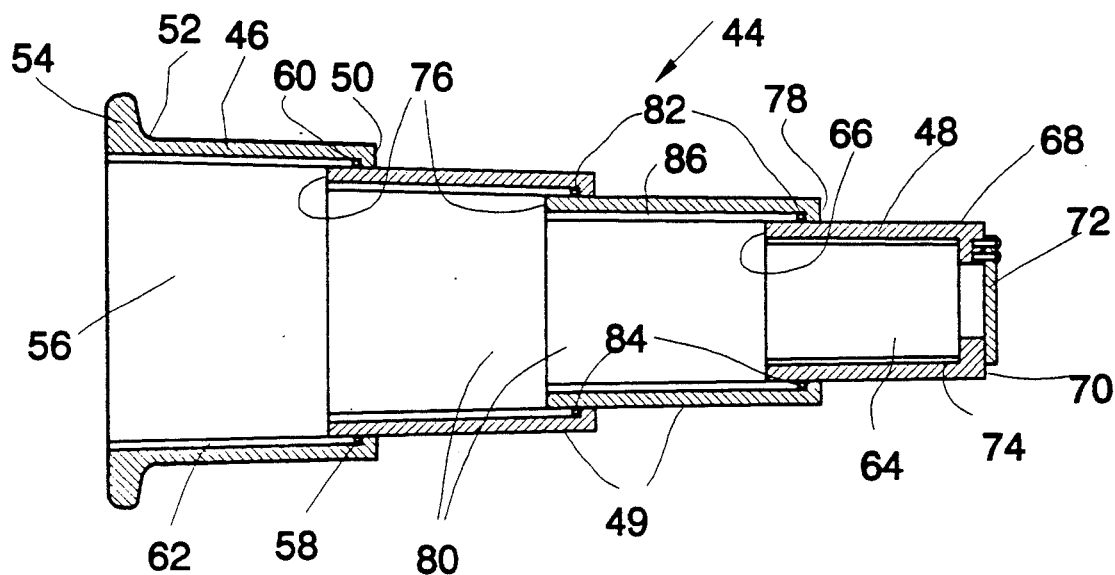
FIGS. 2A and 2B are cross-sectional views of a collapsible condom tester and applicator in an erected configuration according to the present invention.

A cross-sectional view of a collapsible tester and applicator in an erected configuration according to the present invention is shown in FIG. 2A.

The collapsible tester and applicator comprises a telescopically foldable cylinder 44 having a proximal conical element 46, a distal conical element 48, and a plurality of medial conical elements 49. Elements 46, 48, and 49 are made of a transparent material, such as clear plastic. Element 46 possesses a tapered end 50, a flared end 52 which contains a mounting flange 54 at its periphery, and a through central opening 56. An O-ring 58 is located in an annular groove 60 which is formed in the interior of element 46 at its tapered end. A plurality of longitudinal grooves 62 is situated in the inner surface of element 46. Grooves 62 connect with and are the same depth as groove 60.

Distal element 48 possesses a blind central opening 64, a flared end 66, and a tapered end 68, which contains an end-face 70 having a flap-type one-way check valve 72, similar to valve 18 of FIG. 1D. A plurality of longitudinal grooves 74 is situated in the interior surface of element 48.

Conical elements 49 each have a flared end 76, a tapered end 78, and a through central opening 80. An O-ring 82 is located in an interior annular groove 84 positioned near tapered end 78 of each medial conical element. A plurality of longitudinal grooves 86 is formed in the interior of each element 49. Grooves 86 connect with and have the same depth as groove 84.

Manual bellows 88, connected to a cylindrical cap 90 through a flexible tube 92, may be utilized in conjunction with cylinder 44 instead of inflation cap 26, described in connection with the first embodiment of the invention. An O-ring 94 is recessed in an annular groove 96, which is located in the inner surface of cap 90, and provides an air-tight fit between cap 90 and the tapered end of distal element 48.

In one specific embodiment of the invention, cylinder 44 is approximately 20 cm long in its unfolded state and consists of about 4 conical sections. The outside diameter of the flared end of element 46 is approximately 7.5 cm and the outside diameter of the tapered end of element 48 is approximately 5.5 cm.

FIGS. 1, 2 through 2A—Collapsible Condom Tester and Applicator—Operation

To test and apply the condom, the user erects the collapsed tester and applicator (FIG. 2C) by pulling elements 46 and 48 in the opposite directions until the conical elements of cylinder 44 interlock with one another to provide an air-tight seal (FIG. 2A). The seal between the conical elements of cylinder 44 is produced due to the engagement between the conical surfaces of elements 46, 48, and 49, and due to the sealing effect provided by O-rings 58 and 82.

Figure 2B:
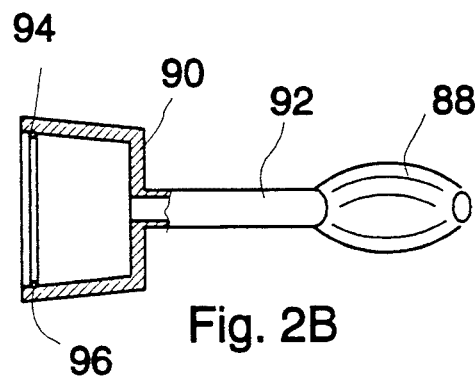
Figure 2C:
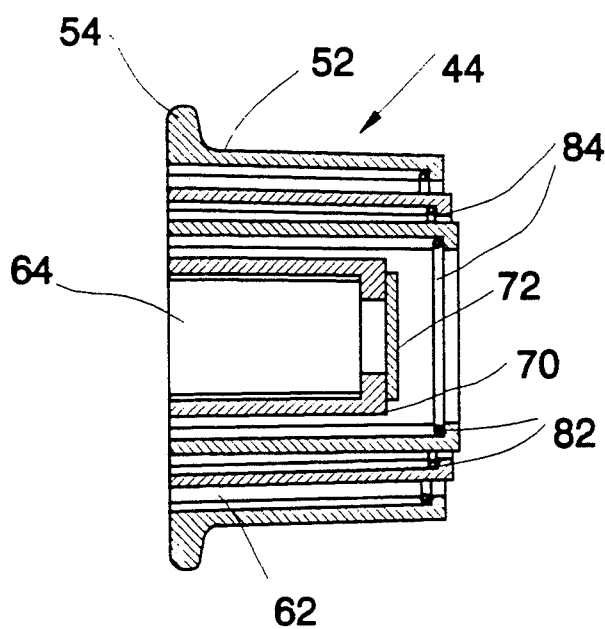
FIG. 2C is a cross-sectional view of a collapsed condom tester and applicator of FIG. 2A.

Otherwise, the testing and application procedure is identical to that described in the previous operation section, except that manual bellows 88 (FIG. 2B) may be utilized to inflate a condom instead of cap 26 (FIG. 1B). To force air into a condom (not shown) which has been installed into cylinder 44, bellows 88 is constricted while cap 90 is sealingly attached to element 48 (FIG. 2). Bellows 88 is then released, creating a pressure differential across the condom sheath and thus distending the condom.

The collapsible construction of the condom tester and applicator considerably facilitates storage and transportation of the device.

Figure 3:
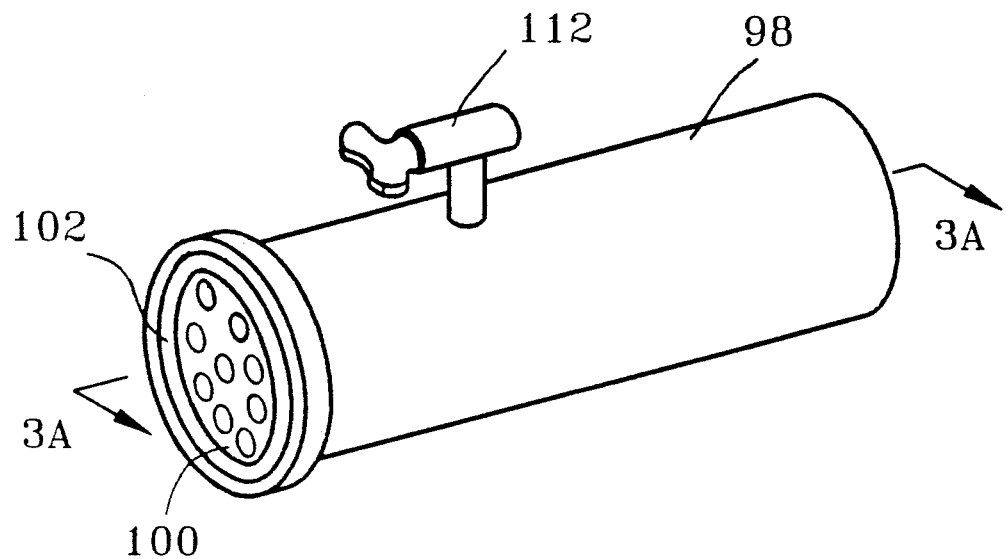
FIG. 3 is a perspective view of a condom tester and applicator with a removable core according to the present invention.
Figure 3A:
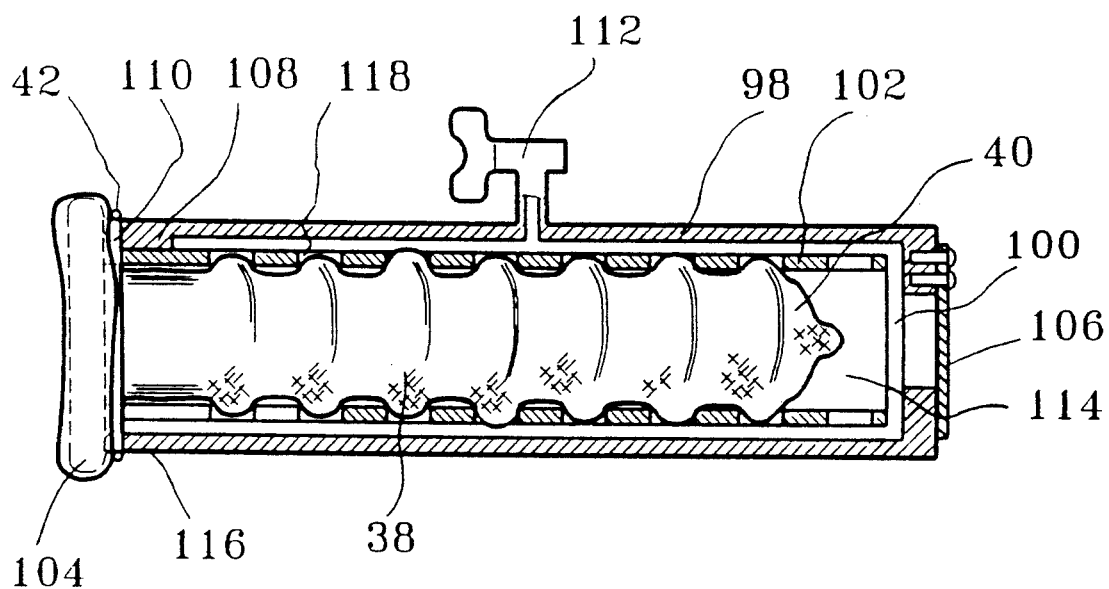
FIG. 3A is a cross-sectional view of the tester and applicator of FIG. 3 taken in the direction indicated by lines 3A—3A of FIG. 3.

FIGS. 3 and 3A—Condom Tester and Applicator with Removable Core—Description

A perspective view of a condom tester and applicator with a removable core according to the present invention is shown in FIG. 3.

The condom tester and applicator comprises a hollow cylinder 98 having a blind central opening 100, which contains a removable perforated cylindrical core 102. Cylinder 98 and core 102 are made of a transparent material, e.g., clear plastic.

A cross-sectional view of the condom tester and applicator with a removable core is shown in FIG. 3A.

Cylinder 98 contains a mounting flange 104 at its proximal end and a flap-type one-way check valve 106 at its distal end. A raised annular portion 108 is located on the inner surface of cylinder 98 at its proximal end. Portion 108 possesses a conical chamfer 110. A lubrication valve 112 is situated in the body of cylinder 98. Core 102 contains a through central opening 114, a conical flared portion 116, and a plurality of test openings 118.

In one specific embodiment of the invention, the outer diameter of core 102 is approximately 6 cm and the diameter of core perforations is about 5 mm. The outer diameter of cylinder 98 is approximately 7.5 cm.

FIGS. 1, 2, 3, and 3A—Condom Tester and Applicator with Removable Core—Operation To test and apply a condom, the user inserts unrolled condom sheath 38 into core 102 and hem ring 42 of sheath 38 is then sealingly wrapped around flange 104. Before testing and application, it is possible to lubricate the unrolled condom though valve 112.

Sheath 38 is then distended, either by forcing air into the proximal end of cylinder 98 through cap 26 (FIG. 1B), or by applying suction to the distal end of cylinder 98 with bellows 88 (FIG. 2B). As sheath 38 is inflated, portions of the sheath are forced through openings 118, further stretching the membrane of the condom. The additional stretching of the condom membrane will expose even minute defects of sheath 38 which would otherwise be undetected.

To apply the condom, the user performs the steps identical to those described in the first embodiment of the invention.

The dual-member structure of the above-described condom tester and applicator provides additional accuracy in testing a condom sheath for contraceptive purposes and also reduces the user's risk of incurring a sexually transmitted disease.

Figure 4:
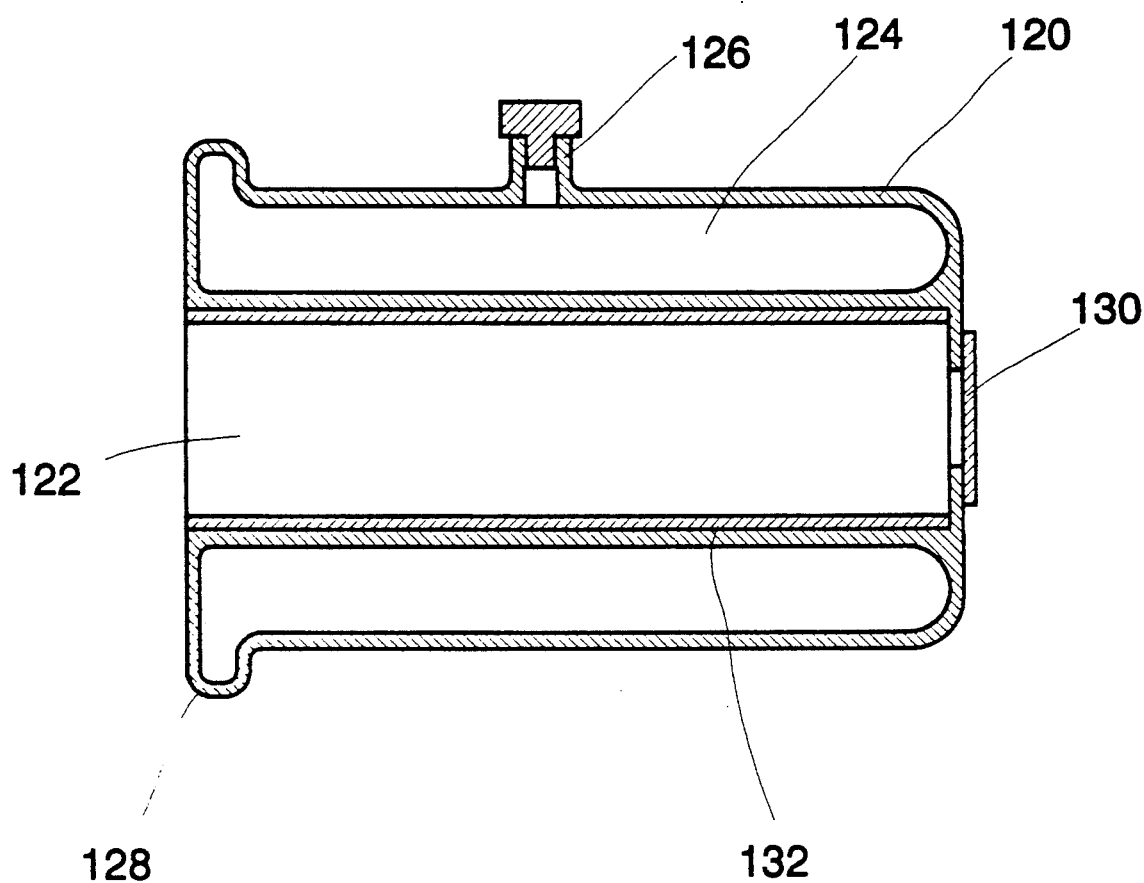
FIG. 4 is a cross-sectional view of a deflatable condom tester and applicator in an inflated state according to the present invention.

FIG. 4—Deflatable Condom Tester and Applicator—Description

A cross-sectional view of a deflatable condom tester and applicator in an inflated state according to the present invention is shown in FIG. 4.

The inflatable condom tester and applicator comprises a cylindrical member 120 having a blind central opening 122 and an air chamber 124, which is supplied with air via a nipple 126. Member 120 is constructed from a transparent air-tight sheath made of a material such as polyvinyl chloride or polyethylene. The proximal end of member 120 possesses a mounting flange 128 and the distal end contains a flap-type one-way valve 130. The inner surface of opening 122 accommodates a plurality of raised longitudinal strips 132.

In one specific embodiment of the invention, member 120 is approximately 20 cm long and is about 7 cm in diameter. Strips 132 protrude approximately 1.5 mm above the surface of opening 122.

FIG. 4—Deflatable Condom Tester and Applicator—Operation

To test and apply a condom, the user first inflates chamber 124 by blowing air into nipple 126. Once the tester is erected, a condom sheath (not shown) is inserted inside opening 122 and the hem ring of the condom (also not shown) is sealingly wrapped around flange 128.

Otherwise, the condom testing and application procedure is identical to that described in the previous embodiments of the invention.

The deflatable construction of the above-described condom tester and applicator allows the tester to be transported and stored in a exceptionally compact form.

SUMMARY, RAMIFICATIONS, AND SCOPE

Thus, it has been shown that I have provided a condom tester and applicator which quickly and accurately tests the integrity of a condom sheath, which allows the user to apply a condom instantaneously, which suspends a tested condom in a state ready for immediate application, which has a compact and simple construction, which is convenient in use, and which is easy and inexpensive to manufacture.

Although the condom tester and applicator has been described in the form of several specific embodiments, its parts, materials, and configurations are given only as examples, and many other modifications of the device are possible. The tester and applicator may be made of different materials, e.g., polyvinyl chloride or polyethylene. Moreover, the tester and applicator may be manufactured in different lengths and sizes. The longitudinal channels and raised strips which allow the air pockets to expel may be angularly oriented. The openings in the perforated core of one of the embodiments of the invention may be round, elliptical, square, or may have any other shape. Instead of a perforated core, a wire-mesh core may be utilized. The one-way check valve of the tester and applicator may be substituted with a through opening which could be manually controlled by the user in order to maintain a pressure differential across the condom membrane to test the condom. A manual shut-off valve may also be employed instead of a one-way valve.

Therefore, the scope of the invention should be determined, not by the examples given, but by the appended claims and their legal equivalents.

What I claim is:

1. A method for testing a condom sheath which has an elastic membrane and a hem ring, comprising:
   providing a tester and applicator having an interior chamber with a working surface, an open proximal end, and a distal end, said proximal end containing installing means for sealingly mounting said hem ring, said distal end accommodating valve means for expelling air from said interior chamber;
   creating a variable-volume chamber inside said interior chamber of said tester and applicator by inserting said elastic membrane inside said interior chamber and sealingly mounting said hem ring onto said installing means;
   testing said condom sheath for possible flaws by expelling air from said variable-volume chamber through said valve means, whereby said elastic membrane distends to expose said possible flaws;
   expelling air trapped between said elastic membrane and said working surface of said interior chamber; and
   donning said condom sheath onto a penis having a base portion by:
     inserting said penis into said condom sheath, said condom sheath being inflatably installed within said interior chamber;
     dislodging said hem ring from said installing means and positioning said hem ring around said base portion of said penis;
     removing said penis with said condom sheath from said interior chamber; and
     expelling air which may be trapped between said elastic membrane and said penis by inserting a tube between said penis and said condom sheath prior to donning said condom sheath onto said penis.

2. A method for testing a condom sheath which has an elastic membrane and a hem ring, comprising:
   providing a tester and applicator having an interior chamber with a working surface, an open proximal end, and a distal end, said proximal end containing installing means for sealingly mounting said hem ring, said distal end accommodating valve means for expelling air from said interior chamber;
   creating a variable-volume chamber inside said interior chamber of said tester and applicator by inserting said elastic membrane inside said interior chamber and sealingly mounting said hem ring onto said installing means; and
   testing said condom sheath for possible flaws by expelling air from said variable-volume chamber through said valve means, whereby said elastic membrane distends to expose said possible flaws;
   said testing said condom sheath being performed by inflating said condom sheath through a mouthpiece sealingly attachable to said proximal end of said tester and applicator.

3. The method recited in claim 2 wherein said installing means comprises a mounting flange.

4. The method recited in claim 2 wherein said valve means comprises a one-way check valve.

5. The method recited in claim 2 wherein said interior chamber has an inner diameter about 1.5 times greater than the outer diameter of said penis.

6. The method recited in claim 2 wherein said step of testing said condom sheath is performed by applying a vacuum to said valve means via a manually powered bellows.

7. An apparatus for testing and applying onto a penis a condom sheath which possesses an elastic membrane and a hem ring, comprising:
   an elongated member possessing an interior chamber, an open proximal end, and a distal end, said interior chamber having an inner surface;
   installing means for sealingly mounting said hem ring located at said open proximal end;
   valve means for expelling air from said inner chamber situated at said distal end; and
   air-channelling means for ejecting air which may be trapped between said elastic membrane and said inner surface of said interior chamber, said air-channelling means being located on said inner surface of said interior chamber.

8. The apparatus of claim 7 wherein said elongated member is a transparent cylinder having a blind central opening.

9. The apparatus of claim 8 wherein said transparent cylinder is made of clear plastic.

10. The apparatus of claim 7 wherein said installing means comprises a mounting flange.

11. The apparatus of claim 7 wherein said valve means comprises a one-way valve.

12. The apparatus of claim 7 wherein said air-channeling means comprises at least one longitudinal groove.

13. The apparatus of claim 7 further including manual means for creating a pressure differential across said condom sheath.

14. The apparatus of claim 13 wherein said manual means comprises a mouthpiece sealingly attachable to said proximal end of said elongated member.

15. The apparatus of claim 13 wherein said manual means comprises a bellows sealingly attachable to said proximal end of said elongated member.

16. The apparatus of claim 7 further including insertable means for expelling air which may be trapped between said condom sheath and said penis after the application of said condom sheath onto said penis.

17. The apparatus of claim 16 wherein said insertable means comprises a pliant tube, said tube having a greater length than said elongated member.

18. An apparatus for testing and applying a condom sheath, comprising:
   a collapsible transparent member composed of a plurality of telescopic conical elements, said telescopic conical elements being sealingly interconnected, said collapsible member having an open proximal end and a distal end, each of said telescopic conical elements having an interior surface;
   a mounting flange located at said open proximal end;
   a one-way valve situated at said distal end; and
   at least one air-channelling groove located in said interior surface of each one of said telescopic conical elements.

19. An apparatus for testing and applying a condom sheath, comprising:
- a transparent cylinder having an inner chamber, an open proximal end, and a distal end;
- a transparent test cylinder having a through central opening and a plurality of perforations, said transparent test cylinder being removably inserted into said inner chamber;
- a mounting flange located at said open proximal end; and
- a one-way valve situated at said distal end.

20. The apparatus of claim 19 further including a lubrication valve mounted into said transparent rigid cylinder.

21. An apparatus for testing and applying a condom sheath, comprising:
- a pliant transparent cylinder having an inflatable chamber, a blind central opening, an open proximal end, and a distal end, said blind central opening having an interior surface;
- a mounting flange located at said open proximal end;
- a nipple attached to said pliant transparent cylinder, said nipple being connected with said inflatable chamber;
- a one-way flap-type valve situated at said distal end; and
- at least one continuous raised strip placed on said interior surface of said blind central opening.

* * * * *